United States Patent

Kurc

(10) Patent No.: US 6,942,669 B2
(45) Date of Patent: Sep. 13, 2005

(54) DRILLING DEVICE COMPRISING A BONE RECUPERATING TREPHINE

(76) Inventor: Michel Kurc, 122, Avenue de la Republique, Paris (FR), 75011

(*) Notice: Subject to any disclaimer, the term of this patent is extended or adjusted under 35 U.S.C. 154(b) by 147 days.

(21) Appl. No.: 10/416,223

(22) PCT Filed: Nov. 21, 2001

(86) PCT No.: PCT/FR01/03663
§ 371 (c)(1),
(2), (4) Date: May 8, 2003

(87) PCT Pub. No.: WO02/41792
PCT Pub. Date: May 30, 2002

(65) Prior Publication Data
US 2004/0030343 A1 Feb. 12, 2004

(30) Foreign Application Priority Data
Nov. 23, 2000 (FR) .............................................. 00 15131

(51) Int. Cl.⁷ .............................................. A61B 17/32
(52) U.S. Cl. ...................................................... 606/80
(58) Field of Search .............................. 606/79, 80, 83, 606/84, 96, 99; 623/923; 408/204, 227, 228

(56) References Cited

U.S. PATENT DOCUMENTS

| | | | | |
|---|---|---|---|---|
| 493,730 A | * | 3/1893 | MacKenzie | 606/179 |
| 2,062,257 A | * | 11/1936 | Douglas et al. | 408/204 |
| 2,919,692 A | * | 1/1960 | Ackerman | 600/567 |
| 3,893,445 A | * | 7/1975 | Hofsess | 600/567 |
| 4,512,344 A | * | 4/1985 | Barber | 606/79 |
| 4,543,966 A | * | 10/1985 | Islam et al. | 600/567 |
| 4,649,918 A | * | 3/1987 | Pegg et al. | 606/79 |
| 4,696,308 A | | 9/1987 | Meller et al. | |
| 4,895,146 A | | 1/1990 | Draenert | |
| 5,049,150 A | * | 9/1991 | Cozad | 606/80 |
| 5,331,972 A | | 7/1994 | Wadhwani et al. | 600/567 |
| 5,697,935 A | * | 12/1997 | Moran et al. | 606/104 |
| 5,928,238 A | | 7/1999 | Morris et al. | |
| 6,015,248 A | * | 1/2000 | Elliott et al. | 408/204 |
| 6,110,178 A | | 8/2000 | Zech et al. | |
| 6,139,509 A | | 10/2000 | Stutz et al. | |
| 6,312,432 B1 | * | 11/2001 | Leppelmeier | 606/80 |

FOREIGN PATENT DOCUMENTS

| EP | 0 992 218 | 4/2000 |
|---|---|---|
| EP | 0 995 402 | 4/2000 |

* cited by examiner

*Primary Examiner*—Eduardo C. Robert
*Assistant Examiner*—David Comstock
(74) *Attorney, Agent, or Firm*—Young & Thompson

(57) ABSTRACT

A bone recuperating drilling device includes a trephine in the form of a tube designed to be driven in rotation, open at both ends and provided with teeth on the periphery of its front opening. The trephine is internally equipped with a bone crushing blade which has one end provided with cutting edges extending substantially in the plane of the trephine front opening.

18 Claims, 3 Drawing Sheets

DRILLING DEVICE COMPRISING A BONE RECUPERATING TREPHINE

BACKGROUND OF THE INVENTION

The present invention relates to a drilling device comprising a bone recuperating trephine.

The invention finds a particularly advantageous application in the fields of parodontology, implantology and orthopedics, where there is a demand for recuperation of bone from a patient to perform bone grafts or to be used as a filling material.

In the conventional way, the bone recuperating trephine takes the form of a tube designed to be driven in rotation, comprising, at its front end, an opening provided with teeth on its periphery. The trephine is closed at its rear end and is connected to a stem, which can be in one piece with it, for mounting it in a brace or on a hand-piece, and is driven in rotation at a low speed.

The main drawback of the above kind of trephine is that the bone core taken with it cannot be used directly. The core must be removed from the trephine and manipulated with various instruments. These manipulations of the bone sample to transfer it can unfortunately lead to it being contaminated with external contaminants.

The document U.S. Pat. No. 5,928,238 discloses a surgical drilling device which includes a conventional bone recuperating trephine as described above, through which passes a longitudinal rod that has, at its free end, a point that extends beyond said opening of the trephine provided with teeth.

This point is anchored in the bone to be drilled to prevent the trephine skidding when it is cutting into the bone.

Apart from the fact that the above drilling device can only produce a bone core that is not crushed, it has the drawbacks previously cited in connection with the bone recuperating trephine.

Furthermore, there currently exist various devices for obtaining crushed bone. Some of these devices comprise, on the one hand, a cutter, and, on the other hand, a crushed bone recuperating device consisting of a filter incorporated into a surgical suction device.

During drilling with irrigation, the surgical suction device operates to recover the bone chips at the outlet from the drilling hole. These bone chips, which constitute the crushed bone, are separated out by the filter of the surgical suction device.

When taking bone samples from the inside of the buccal cavity, the above kind of crushed bone recuperating device can collect contaminants coming from the saliva.

Other devices for obtaining crushed bone incorporate a cutter blade and a filter in the surgical suction device. The main drawbacks of devices of this kind are that they can also recover bone material with contaminants and are particularly bulky.

Because of their bulkiness, the above devices cannot be used to take bone samples from the rear of the buccal cavity, and can be used only at the front.

Furthermore, as a general rule, the above devices are relatively complex, which increases their fabrication cost.

Finally, the document EP 0 992 218 discloses a biopsy device for taking bone samples and comprising a bone recuperating trephine that is mobile in translation, not in rotation, and is equipped internally with a bone crushing blade that extends longitudinally along the axis of the trephine and has a cutting end extending beyond the opening of the trephine.

Once the biopsy device has been introduced into the bone of the patient, the trephine is held fixed and the bone crushing blade is driven in rotation inside the trephine to produce crushed bone.

Because the end of the crushing blade extends beyond the opening of the trephine, the trephine and the blade of the biopsy device described in the document EP 0 992 218 cannot be operative simultaneously to produce a bone core sample.

SUMMARY OF THE INVENTION

To overcome all of the drawbacks cited above, the present invention proposes a bone recuperating drilling device comprising a trephine in the form of a tube designed to be driven in rotation, open at both ends and provided with teeth on the periphery of its front opening, characterized in that the trephine is internally equipped with a bone crushing blade which comprises one end provided with cutting edges extending substantially in the plane of the front opening of the trephine.

Thus, the bone recuperating trephine of the drilling device according to the invention can advantageously be used directly, without any operation to transfer the bone sample to a bone injection syringe for reimplanting the sampled bone at an appropriate location on the skeleton of a patient.

To this end, an advantageous feature of the trephine of the drilling device according to the invention is that it is adapted to be removably mounted at the end of a cylindrical passage in which slides the piston rod of a bone injection syringe.

Furthermore, in the drilling device according to the invention, the trephine and the bone crushing blade are operative simultaneously to produce the crushed bone core without the sampled bone being contaminated by contaminants and without blocking the entry of the trephine.

Using the drilling device according to the invention, the core extracted by the trephine is immediately crushed by the blade, the crushed bone progressively filling the trephine tube.

In a preferred embodiment of the drilling device according to the invention, said blade extends longitudinally along the axis X of the trephine.

Said blade can advantageously include a spike centered between the two cutting edges previously cited and extending to the exterior of the trephine to guide the trephine while drilling.

This blade is preferably part of a cutter adapted to be removably mounted on the trephine and including a rotation driving stem, at the end of which the trephine is mounted, fastened to said blade, and extending in a direction opposite to the blade.

Thus, after a crushed bone core sample has been taken, the cutter can be uncoupled from the trephine which, containing the crushed bone, can be mounted on a bone injection syringe, as previously explained.

The stem of the cutter of the drilling device previously cited advantageously includes an internal irrigation bore over the whole of its length and possibly extending into a median opening of said U-shaped blade.

In one embodiment, the trephine is removably mounted on the cutter by pin means.

In another embodiment, the trephine is removably mounted on the cutter by bayonet means.

In another embodiment, the trephine is removably mounted on the cutter by clip means.

In another embodiment, the trephine is removably mounted on the cutter by screw means.

In another embodiment of the drilling device according to the invention, said blade extends longitudinally and globally transversely to the axis X of the trephine.

Said blade can then be in one piece with the trephine and situated in the vicinity of the front end of the trephine.

The following description, which is given with reference to the accompanying drawings, which are provided by way of non-limiting example, explains in what the invention consists and how it can be put into effect.

DETAILED DESCRIPTION OF THE PREFERRED EMBODIMENTS

Firstly, note that identical or similar parts of the various embodiments of the invention shown in the various figures are wherever possible identified by the same reference symbols and are not described again each time.

Figure 1:
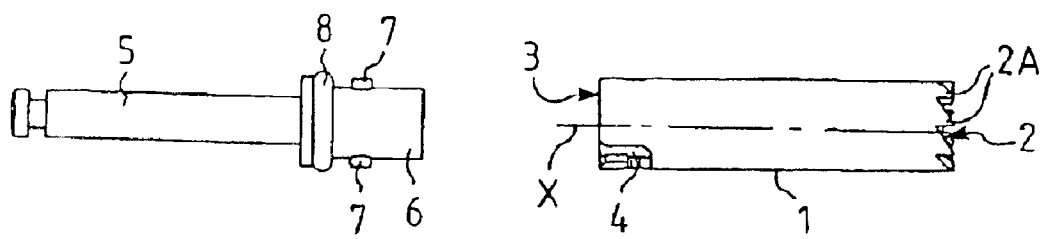
FIG. 1 is a diagrammatic side view of a bone recuperating trephine according to the invention and an associated rotation drive stem.

FIG. 1 shows a bone recuperating trephine 1 which takes the form of a tube having an axis X and adapted to be driven in rotation, in particular by a stem 5. The trephine 1 comprises, at its front end, an opening 2 provided on its periphery with teeth 2A for cutting into the bone of a skeleton of a patient during drilling to take a bone core sample.

The trephine 1 also has an opening 3 at its rear end.

Its rear portion, adjacent the opening 3, includes means for removably mounting it on the end 6 of the stem 5. The stem 5 can be coupled to a brace or to a hand-piece (not shown) and driven in rotation at a low speed to perform a drilling operation.

Here the mounting means are bayonet means, comprising two grooves 4 on the trephine 1, symmetrically positioned relative to the axis X, and opening onto the edge of the opening 3 of the trephine, the grooves 4 being conformed for quarter-turn mounting on two correspondingly positioned studs 7 at the end 6 of the stem 5.

Figure 5:
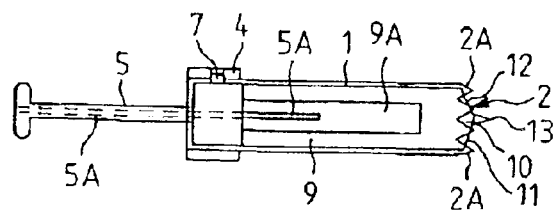
FIG. 5 is a diagrammatic side view of a second embodiment of a drilling device according to the invention, showing the internal components thereof as if it were transparent.
Figure 8:
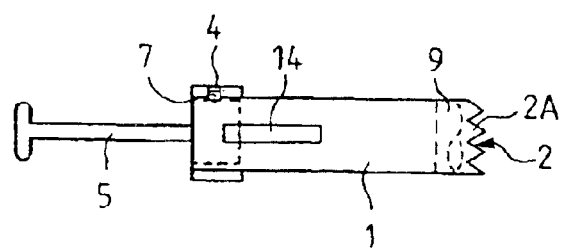
FIG. 8 is a diagrammatic view of a third embodiment of a drilling device according to the invention, showing the internal components thereof as if it were transparent.

Of course, the means for removably mounting the trephine 1 on the stem 5 can, in different embodiments, such as that shown in FIGS. 5 and 8, be pin means comprising a housing 4 at the rear end of the trephine 1 designed to cooperate with a pin 7 provided at the end of a stem 5, the pin 7 being spring-loaded by a spring, not shown.

In other variants, not shown, the mounting means can be of the clip or screw type.

Moreover, as can be seen in FIG. 1, a seal 8 is provided at the junction between the rear portion of the stem 5 and its mounting end 6, in this example a circular seal, threaded over it to establish a sealed junction between the trephine 1 and the stem 5 at the rear opening 3 of the trephine 1.

Figure 2:
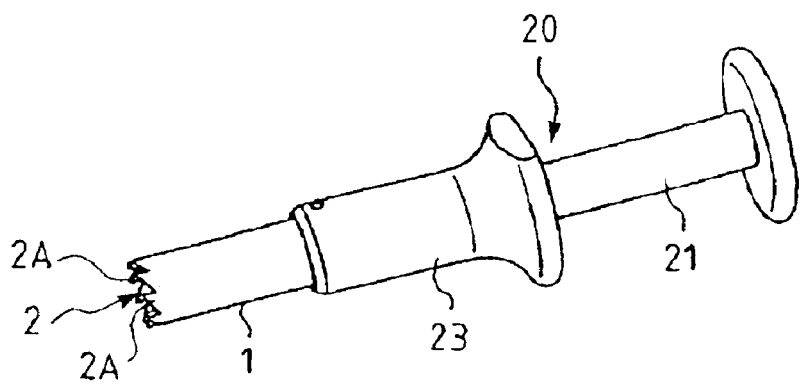
FIG. 2 is a diagrammatic perspective view of the trephine from FIG. 1 mounted on a cylindrical passage of a bone injection syringe.

As can be seen in FIG. 2 in particular, the trephine 1 is advantageously adapted to be removably mounted at the end of a cylindrical passage 23 in a bone injection syringe 20, by means of the removable mounting means, previously described, for mounting the trephine 1 on the mounting end 6 of the stem 5.

The trephine 1 extends the cylindrical passage 23 of the bone injection syringe 20 in the axial direction. The syringe further includes a piston rod 21 which slides in the cylindrical passage 23 to inject into the bone receiving site of a patient the crushed bone accumulated in the trephine 1.

The means provided on the trephine for removably mounting it at the end of the cylindrical passage of a bone injection syringe are generally also used to mount it on a stem connected to a rotation drive system.

A trephine 1 for use in dental surgery has an outside diameter from approximately 3 to approximately 8 millimeters and a length equal to approximately 20 millimeters. Of course, it can have a greater diameter and length for use in orthopedic bone surgery, where the bone samples can be much larger.

Figure 3:
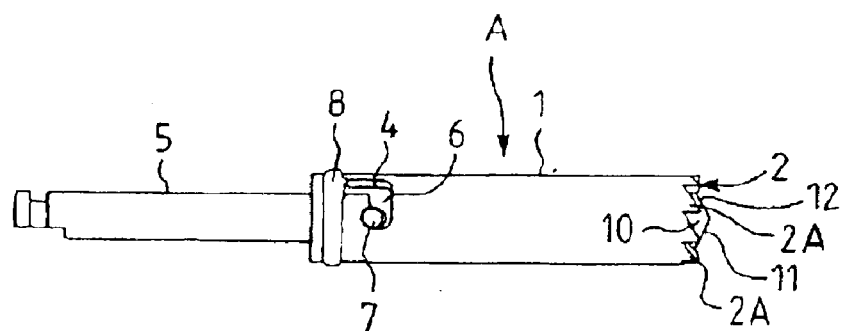
FIG. 3 is a diagrammatic side view of a first embodiment of a drilling device according to the invention.
Figure 4:
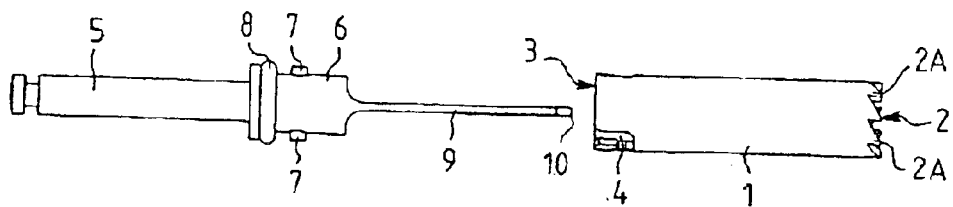
FIG. 4 is a diagrammatic exploded side view of the drilling device shown in FIG. 3.

FIGS. 3 and 4 show more particularly a bone recuperating drilling device A which includes the trephine 1 shown in FIG. 1, previously described and equipped internally with a bone crushing blade 9.

The thin blade 9 extends longitudinally along the axis X of the trephine and has an end 10 provided with two cutting edges 11, 12 forming a point in the plane of the front opening 2 of the trephine 1.

The blade 9 is part of a cutter adapted to be removably mounted on the trephine, by the bayonet mounting means 4, 7 previously described, and including a rotation drive stem 5, at the end 6 of which the trephine 1 is removably mounted, attached to said blade 9 and extending in the opposite direction thereto.

In this instance the blade 9 and the stem 5 are in one piece.

As in FIG. 1, a seal 8 is threaded over the end 6 of the stem 5 to improve the seal at the rear opening 3 of the trephine 1 when the latter is mounted on the stem 5.

Figure 6:
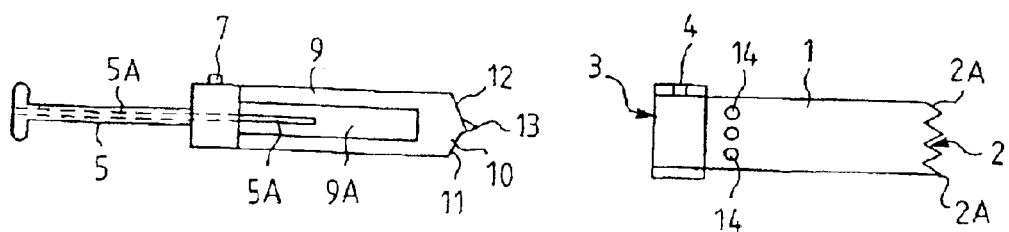
FIG. 6 is a diagrammatic exploded side view of the drilling device from FIG. 5.
Figure 7:
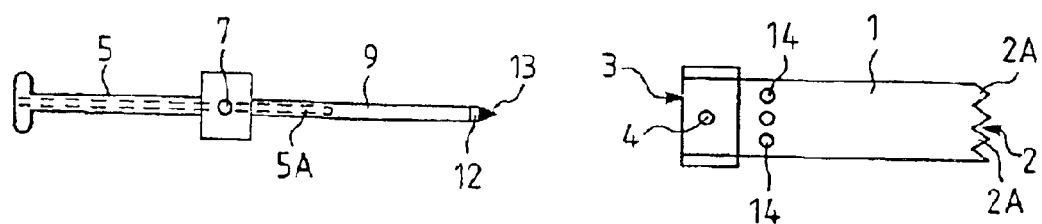
FIG. 7 is a diagrammatic view of the drilling device from FIG. 6 from another side, showing the edge of the blade.

FIGS. 5 to 7 show a different embodiment of the drilling device shown in FIGS. 3 and 4, wherein the blade 9, which extends longitudinally along the axis X of the trephine, and which is part of a cutter adapted to be removably mounted on the trephine, takes the form of a U-shape whose branches are joined to the end of the stem 5 and define a median opening 9A between them.

In this instance, the stem 5 is connected temporarily to the trephine 1 by pin mounting means 4, 7.

Furthermore, the stem 5 shown in FIGS. 5 and 6 includes an internal irrigation bore 5A over the whole of its length and which in this instance extends into the interior of the median opening 9A of said U-shaped blade 9.

Figure 9:
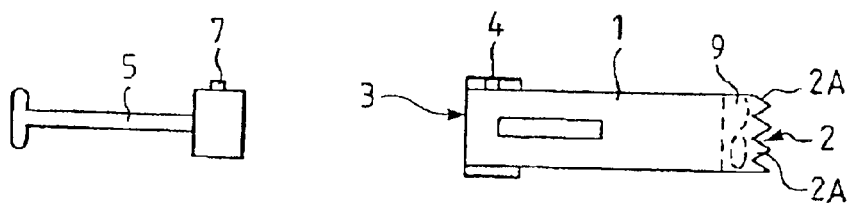
FIG. 9 is a diagrammatic exploded side view of the drilling device shown in FIG. 8.

On the subject of irrigation, an advantageous feature of the trephine 1 according to the invention is that it can include, in the vicinity of its rear end, irrigation bores 14, such as perforations (see FIGS. 6 and 7) or slots (see FIGS. 8 and 9).

The blade 9 shown in FIGS. 5 and 6 has at its end 10 provided with two cutting edges 11 and 12 a spike 13 centered between the two cutting edges 11 and 12 and extending to the exterior of the trephine 1 to guide the trephine 1, and more generally the drilling device, when drilling.

FIGS. 8 and 9 show another embodiment of a drilling device according to the invention, including the trephine 1 containing a blade 9 which extends longitudinally and globally transversely to the axis X of the trephine.

In this instance, the blade 9 is generally helical in shape, but it can have any other suitable shape, such as a cruciform or other shape.

The rotation drive stem 5 is removably mounted on the trephine 1 by means of the pin mounting means 4, 7 previously described.

The blade 9 is advantageously in one piece with the trephine 1 and is situated in the vicinity of the front end of the trephine 1 provided with the opening 2.

As previously described, at the rear, the trephine 1 includes an irrigation bore 14 in the form of slots.

The trephine 1, its stem 5 and the blade 9 are generally made from biocompatible materials such as hardened stainless steel, for example.

The core sample taken by the trephine of the drilling device shown in the various figures is advantageously crushed immediately by the blade and the crushed bone progressively fills the trephine.

After filling the trephine, the stem of the drilling device can be uncoupled from the brace and the crushed bone can be injected directly by coupling the trephine to the bone injection syringe 20 shown in FIG. 2.

There is then no longer any problem with transferring the crushed bone or with possible contamination thereof during transfer.

The present invention is in no way limited to the embodiments described and shown, variations of which conforming to the spirit of the invention will be evident to the person skilled in the art.

What is claimed is:

1. A bone recuperating drilling device comprising:
    a trephine in the form of a tube designed to be driven in rotation, open at both ends and provided with teeth on the periphery of its front opening; and
    a bone crushing blade internal to said trephine, said bone crushing blade is fixed in rotation with said trephine and has one end provided with cutting edges, said cutting edges extend substantially in the plane of the front opening of the trephine so that the bone crushing blade and the trephine are adapted to operate simultaneously in order that a core sample extracted by said trephine is immediately crushed by said blade and a crushed bone progressively fills said trephine.

2. The drilling device according to claim 1, wherein the blade extends longitudinally along a longitudinal axis of the trephine.

3. The drilling device according to claim 1, wherein said blade is part of a cutter adapted to be removably mounted on the trephine and including a rotation stem, at the end of which the trephine is mounted, fastened to said blade, and extending in an opposite direction thereto.

4. The drilling device according to claim 3, wherein said stem has an internal irrigation bore over the whole of its length.

5. The drilling device according to claim 4, wherein said blade has a U-shape with a median opening, said internal irrigation bore of the stem extending into an interior of said median opening.

6. The drilling device according to claim 3, wherein the trephine is removably mounted on the cutter by pin means.

7. The drilling device according to claim 3, wherein the trephine is removably mounted on the cutter by bayonet means.

8. The drilling device according to claim 3, wherein the trephine is removably mounted on the cutter by clip means.

9. The drilling device according to claim 3, wherein the trephine is removably mounted on the cutter by screw means.

10. The drilling device according to claim 1, wherein said blade includes a spike centered between two of said cutting edges and extending to an exterior of the trephine to guide the trephine during drilling.

11. The drilling device according to claim 1, wherein said blade extends longitudinally and globally transversely to the longitudinal axis of the trephine.

12. The drilling device according to claim 11, wherein said blade is in one piece with the trephine.

13. The drilling device according to claim 1, wherein the trephine includes irrigation bores, such as slots or perforations, in the vicinity of its rear end.

14. A bone recuperating drilling device, comprising:
    a cylindrical trephine structured and arranged to be driven in rotation, said trephine being open at first and second ends and having a plurality of teeth on a periphery of said first end, said second end having at least one female mounting member; and
    a cutting member having a bone crushing blade extending within said trephine, a distal end of said blade having cutting edges that extend substantially in a same plane as said first end of said trephine,
    said cutting member having at least one male mounting member immediately adjacent a proximal end of said blade and releasably engaging said at least one female mounting member.

15. The drilling device according to claim 14, wherein said blade is U-shaped with legs of the U being at the proximal end of said blade.

16. The drilling device according to claim 14, wherein said trephine comprises irrigation bores adjacent said second end.

17. The drilling device according to claim 16, wherein said bores are one of slots and perforations.

18. A bone recuperating drilling device, comprising:
    a cylindrical trephine structured and arranged to be driven in rotation, said trephine being open at first and second ends and having a plurality of teeth on a periphery of said first end; and
    a bone crushing blade internal to said trephine and fixed in rotation with said trephine, a distal end of said blade having two cutting edges that extend substantially in a same plane as said first end of said trephine.

* * * * *